US010183068B2

(12) United States Patent
Muttil et al.

(10) Patent No.: US 10,183,068 B2
(45) Date of Patent: Jan. 22, 2019

(54) VACCINATION COMPOSITIONS, METHODS OF MAKING, AND METHODS OF USE

(71) Applicant: STC.UNM, Albuquerque, NM (US)

(72) Inventors: Pavan Muttil, Albuquerque, NM (US); Denis Wafula, Albuquerque, NM (US); Terry Wu, Albuquerque, NM (US); Nitesh Kunda, Albuquerque, NM (US); Dominique N. Price, Albuquerque, NM (US)

( * ) Notice: Subject to any disclaimer, the term of this patent is extended or adjusted under 35 U.S.C. 154(b) by 0 days.

(21) Appl. No.: 15/311,298

(22) PCT Filed: May 15, 2015

(86) PCT No.: PCT/US2015/031124
§ 371 (c)(1),
(2) Date: Nov. 15, 2016

(87) PCT Pub. No.: WO2015/175961
PCT Pub. Date: Nov. 19, 2015

(65) Prior Publication Data
US 2017/0112912 A1    Apr. 27, 2017

Related U.S. Application Data

(60) Provisional application No. 61/994,218, filed on May 16, 2014.

(51) Int. Cl.
*A01N 63/00* (2006.01)
*A61K 39/02* (2006.01)
*A61K 9/16* (2006.01)
*A61K 9/00* (2006.01)
*A61K 39/00* (2006.01)

(52) U.S. Cl.
CPC ............ *A61K 39/02* (2013.01); *A61K 9/1617* (2013.01); *A61K 9/1623* (2013.01); *A61K 9/0075* (2013.01); *A61K 2039/522* (2013.01); *A61K 2039/545* (2013.01); *Y02A 50/405* (2018.01)

(58) Field of Classification Search
CPC ..................................................... A61K 39/02
See application file for complete search history.

(56) References Cited

U.S. PATENT DOCUMENTS

| 2009/0169581 A1 | 7/2009 | Sandrine |
| 2011/0045079 A1* | 2/2011 | Edwards ............. A61K 9/1617 424/489 |
| 2012/0058162 A1 | 3/2012 | Jin et al. |

FOREIGN PATENT DOCUMENTS

| WO | WO 2013/016754 A1 | 2/2013 |
| WO | WO 2015/175961 A1 | 11/2015 |

OTHER PUBLICATIONS

Qingmei et al (Vaccine vol. 27, pp. 1216-1229) (Year: 2009).*
Elmaoued et al (Pharmacotherapy vol. 33, No. 10, pp. e298-e299) (Year: 2013).*
International Patent Application No. PCT/US2015/031124, dated May 15, 2015; International Search Report and Written Opinion dated Jul. 27, 2015; 16 pages.
International Patent Application No. PCT/US2015/031124, dated May 15, 2015; International Preliminary Report on Patentability dated Dec. 1, 2016; 11 pages.
Grasmeijer et al., "A User-Friendly Model for Spray Drying to Aid Pharmaceutical Product Development," Sep. 2013, *PLoS ONE* 8(9): e74403, pp. 1-11.
Jia, et al., "Recombinant attenuated *Listeria monocytogenes* vaccine expressing *Francisella tularensis* IgIC induces protection in mice against aerosolized Type A *F. tularensis*," 2009, *Vaccine*, 27(8):1216-1229. Available online Jan. 4, 2009.
Sou, et al., "The effect of amino acid excipients on morphology and solid-state properties of multi-component spray-dried formulations for pulmonary delivery of biomacromolecules," 2013, *European Journal of Pharmaceutics and Biopharmaceutics*, 83:234-243. Available online Nov. 23, 2012.

* cited by examiner

*Primary Examiner* — Albert M Navarro
(74) *Attorney, Agent, or Firm* — Mueting, Raasch & Gebhardt, P.A.

(57) ABSTRACT

This disclosure describes, generally, compositions and methods related to thermostable vaccine formulations, their storage, and their use. Generally, the thermostable vaccine formulations can be in the form of a dry powder. The dry powder formulations can increase the length of time that the vaccine remains viable under non-refrigerated, ambient temperature conditions.

12 Claims, 8 Drawing Sheets

FIG. 6.

**Stability of *Lm* spray dried with different excepients and stored under inert atmospheres**

VACCINATION COMPOSITIONS, METHODS OF MAKING, AND METHODS OF USE

CROSS-REFERENCE TO RELATED APPLICATION

This application is the § 371 U.S. National Stage of International Application No. PCT/US2015/031124, filed 15 May 2015, which claims priority to U.S. Provisional Patent Application Ser. No. 61/994,218, filed May 16, 2014, each of which is incorporated herein by reference.

SUMMARY

This disclosure describes, in one aspect, a vaccine composition that includes a dry powder matrix and a bacterium disposed within the matrix.

In another aspect, this disclosure describes a method of making a vaccine. Generally, the method involves mixing a bacterium that expresses at least one antigen in a solution that comprises at least one amino acid and at least one saccharide and spray drying the mixture to form a dry powder. In some embodiments, the method further includes storing the dry powder vaccine for at least fifteen months under conditions that do not require refrigeration.

In another aspect, this disclosure describes administering a dry powder vaccine to a subject in need of treatment with such a vaccine.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 6. Viability of spray dried *Listeria monocytogenes* (Lm) vaccine (dry powder) stored at 4° C. and 37° C. Only formulation three had CFUs above the detection level ($10^3$ CFU) when stored at 37° C. (without protection) for four weeks. However, an inert atmosphere (high purity $N_2$ gas, $O_2$ scavengers, and desiccant) provided significant protection to the dry powder vaccine at 37° C. that was similar to that observed at 4° C.

DETAILED DESCRIPTION OF ILLUSTRATIVE EMBODIMENTS

Figure 1:
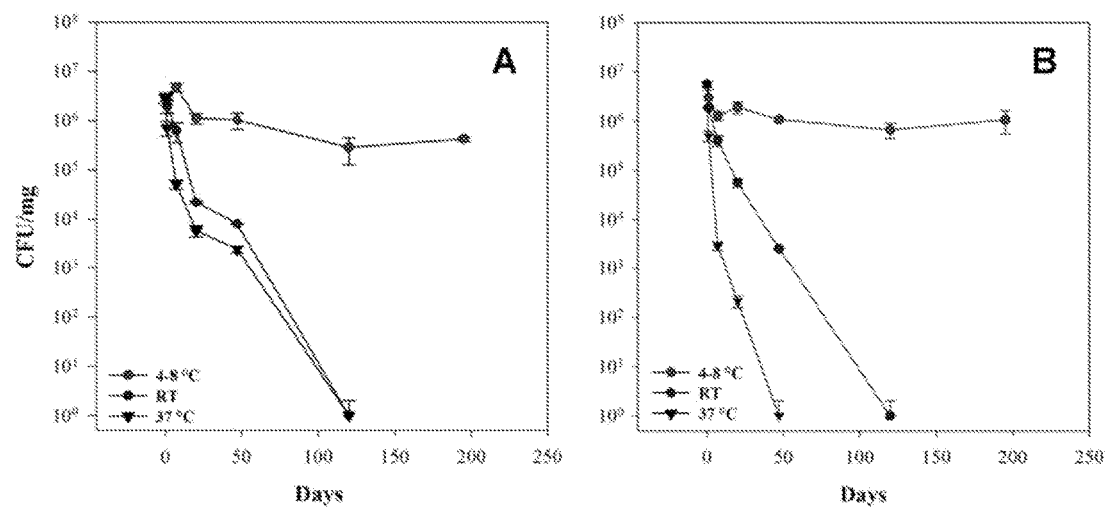
FIG. 1. Viability based on CFUs of non-moisture protected (A) *Listeria monocytogenes* strain 1 and (B) *Listeria monocytogenes* strain 2 dry powder live vaccines at different storage conditions.

This disclosure describes, generally, compositions and methods related to thermostable vaccine formulations, their storage, and their use. Generally, the thermostable vaccine formulations can be in the form of a dry powder. The dry powder formulations can increase the length of time that the vaccine remains viable under non-refrigerated, ambient temperature conditions. The thermostable formulations can allow the transport and storage of the vaccines to areas where refrigeration is unavailable and/or inconvenient such as, for example, military conflict zones, disaster zones, wilderness areas, and certain Third World areas. The formulations can be administered, for example, using needle-free oral and/or pulmonary administration.

As one example, *Francisella tularensis* is a potential biological warfare agent that lacks an approved vaccine. Most vaccine formulations require cold chain storage. Vaccine formulations that can be stored at ambient temperatures are urgently required especially in emergencies or in resource-poor countries. This disclosure describes spray drying to produce a thermostable dry powder live vaccine that also offers flexibility in manner of administration.

While described below in the context of an exemplary embodiment in which attenuated *Listeria monocytogenes* (Lm) carrying tularemia antigens was used as the live vaccine vector, the compositions and methods described herein can be practiced using any suitable bacterial host vector. Suitable bacterial host vectors include, for example, *E. coli*, *Mycobacterium bovis*, *Mycobacterium tuberculosis*, *Salmonella typhi* Ty21a, etc. In addition, the compositions and methods may be practiced by genetically modifying the bacterial vector organism to express one or more antigens of any suitable pathogen. A subject to whom the vaccine composition is administered will generate an immune response against antigen expressed by the bacterial vector organism. The antigen may include one or more endogenous antigens natively expressed by the bacterial vector such as, for example, a secretory antigen. Alternatively, or in addition, the antigen can include one or more heterologous antigens expressed by the bacterial vector organism as a result of being genetically modified. Also, while the exemplary *Listeria monocytogenes* vector is attenuated, in some cases, the bacterial vector may not necessarily be attenuated.

*Listeria monocytogenes* were cultured, re-suspended in a sugar and amino acid solution and then spray dried with the outlet temperatures maintained at 45±2° C. The amino acid and sugar solution was as described in Example 1. Properties of the sugars and amino acids in the solution are summarized in Table 1. Exemplary dry powder compositions are provided in Table 2.

TABLE 1

| Excipient | Properties |
| --- | --- |
| Mannitol | Low hygroscopy |
| Trehalose | Dessico-protectant |
| | High glass transition temperature (Tg) |
| Dextran | Decreases crystallization of spray-dried excipients |
| Leucine | Low hygroscopy and increases flow |
| Inositol | Enhances bacterial survival during spray drying, increases flow |

TABLE 2

| | Formulation composition (% w/w) | | | |
| --- | --- | --- | --- | --- |
| Excipient | 1 | 3 (MTDLI) | 4 | 5 |
| Mannitol | 40 | 85.32 | 61 | 61.12 |
| Trehalose | 10 | 1.71 | 5.29 | 5.3 |
| Dextran | 0 | 0.85 | 0 | 0 |
| Leucine | 20 | 7.85 | 6.75 | 6.76 |
| Inositol | 0 | 4.27 | 3.58 | 3.59 |
| Acacia | 20 | 0 | 23.18 | 23.23 |
| BSA | 10 | 0 | 0.2 | 0 |

The resultant powder compositions were stored at three different temperatures and moisture protection conditions, summarized in Table 3. In some embodiments, the dried amino acid-sugar mixture forms a matrix into which *Listeria monocytogenes* cells are disposed in the spaces of the matrix. Residence of the *Listeria monocytogenes* cells within the matrix promotes viability of the *Listeria monocytogenes* cells. Stability of the powder compositions was assayed using CFU counts. The size and shape of particles were evaluated using laser diffraction and electron microscopy.

TABLE 3

| Storage Conditions | 4-8° C. | Room Temp. (22° C.) | 37° C. |
| --- | --- | --- | --- |
| No moisture protection | ✓ | ✓ | ✓ |
| Moisture protection | ✓ | ✓ | ✓ |
| Moisture protection plus dessicant | ✓ | ✓ | ✓ |

Live vaccine dry powders containing *Listeria monocytogenes* were stored without moisture protection, for at least six months. Samples stored at 4° C. to 8° C. maintained viability with minimal loss of CFUs (FIGS. 1A and 1B).

Moisture protection provided stability, however, at 4° C. and RT, but placing desiccant in direct contact with powders reduced stability. (FIGS. 2A and 2B). At 37° C., desiccant in direct contact with the dry powder vaccine provided better protection than storing the dry powder vaccine in a desiccator alone. Although we observed lower viability than either at 4° C. and RT for the samples stored at 37° C., viability was still observed for over five months (FIGS. 2A and 2B).

The dry powder compositions can be delivered in any suitable route such as, for example, oral ingestion or inhalation. An appropriate particle size for a dry powder composition compatible for deep lung delivery can be between 1-3 µm. The mean volumetric diameter for the dry powders without the live vaccine was 2.25 µm. In addition, scanning electron microscopy demonstrated that *Listeria monocytogenes* live bacterial cells were fully encapsulated by the powders (FIGS. 3A and 3B). Thus, the dry powdered vaccine compositions are appropriate for deep lung inhalation delivery.

We further demonstrated the suitability of compositions for oral ingestion delivery. We evaluated the stability of an enteric coated capsule of in simulated gastric fluid (SGF) and release of its content in simulated intestinal fluid (SIF). Additionally, digestive enzymes were added to SGF and SIF. We used a colorimetric method of evaluation where the capsules were loaded with anhydrous $CuSO_4$. The $CuSO_4$ changes color when in contact with water and thus revealed any loss of capsule integrity in the simulated fluid. FIG. 4A shows the integrity of the enteric coated capsules in acidic media for 50 minutes. FIG. 4B shows the loss of capsule integrity in basic intestinal media.

Figure 5:
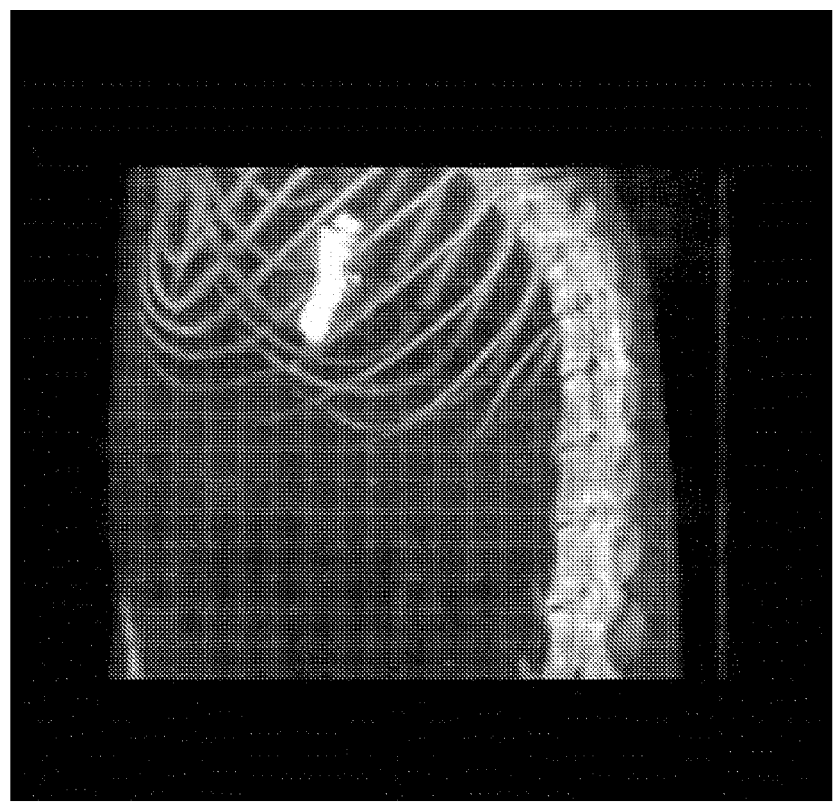
FIG. 5. Enteric coated capsule remaining intact in the stomach of a fasted rat after two hours of exposure to acidic environment. This demonstrates that the contents of the capsule will remain stable in the acidic environment.

Since the live *Listeria monocytogenes* vaccines might be susceptible to being killed in the acidic environment of the stomach when administered for oral ingestion, we have loaded the dry powder vaccines into a size 9 capsule. The capsules were enteric coated in order to delay release of the live *Listeria monocytogenes* vaccine until the capsules reached the intestine. Intestinal release of the live *Listeria monocytogenes* vaccine allows the vaccine to be taken up by the M cells of the intestine, thereby generating an immune response to the antigens expressed by the *Listeria monocytogenes*. We have developed enteric coated capsules with a surrogate dry powder, barium sulfate, that has shown to be intact in the gastric environment of the rat stomach for more than two hours (FIG. 5). We have thus shown that the capsules can provide protection to the live *Listeria monocytogenes* bacterial vaccine in the acidic environment of the stomach and thus be alive when in exits the stomach and reaches the small intestine to be absorbed and ultimately generate an immune response.

Thus, powders stored at 4-8° C. can maintain viability with or without moisture protection for at least 15 months. Vaccine storage at room temperature exhibited more long-term vaccine stability when stored with moisture protection. In addition, the dry powder compositions were of suitable size for pulmonary delivery (FIG. 3A). In addition, we have shown that these thermostable vaccines can be delivered by oral route (needle-free immunization) to generate an immune response against antigen expressed by the vector organism.

The dry powder composition can, therefore, be used to treat a subject. As used herein, "treat" or variations thereof refer to reducing, limiting progression, ameliorating, or resolving, to any extent, the symptoms or signs related to a condition. The treatment may be prophylactic or therapeutic. As used herein, "prophylactic" and variations thereof refer to a treatment that limits, to any extent, the development and/or appearance of a symptom or clinical sign of a condition. "Prophylaxis" refers to any degree of limiting an infection by an infectious agent including (a) preventing or limiting an initial infection, (b) preventing or limiting the spread of an existing infection, or both. "Prophylaxis" may be used interchangeably with "reduce infection" and variations thereof. As used herein, "therapeutic" and variations thereof refer to a treatment that ameliorates one or more existing symptoms or clinical signs associated with a condition. As used herein, "symptom" refers to any subjective evidence of disease or of a patient's condition; "sign" or "clinical sign" refers to an objective physical finding relating to a particular condition capable of being found by one other than the patient.

Thus, the dry composition may be administered to a subject that has or is at risk for an infectious condition. As used herein, "at risk" refers to a subject that may or may not actually possess the described risk. Thus, for example, a subject "at risk" of infection by a microbe is a subject present in an area—or will be entering an area—where individuals have been identified as infected by the microbe and/or is likely to be exposed to the microbe. A subject may be "at risk" even if the subject has not yet manifested any detectable indication of infection by the microbe and regardless of whether the subject may harbor a subclinical amount of the microbe. While the dry powder may formulated, as discussed above, for delivery through oral or pulmonary needle-free immunization routes, the dry powder may be formulated with a pharmaceutically-acceptable carrier for delivery by any suitable route. A pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intravaginal, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

In some cases of, for example, intravenous delivery, the dry powder vaccine may be reconstituted before being administered to a subject by suspending the dry powder in, for example, saline, water, or a buffered solution such as phosphate buffered saline (PBS) so that the bacterium recovers from the dormant state exhibited during storage as a dry powder. The dry powder may be reconstituted a minimum of at least 15 minutes before being administered to a subject such as, for example, at least 30 minutes, at least one hour, at least two hours, at least three hours, at least four hours, or at least six hours before being administered to a subject.

The dry powder may be reconstituted a maximum time of 24 hours before being administered to a subject such as, for example, no more than eight hours, no more than six hours, no more than four hours, no more than three hours, no more than two hours, no more than one hour, no more than 40 minutes no more than 30 minutes, or no more than 20 minutes before being administered to a subject.

In some cases the dry powder may be reconstituted a period of time before being administered to a subject defined by a range having as endpoints any minimum time before being administered to a subject listed above and any maximum time before being administered to a subject listed above that is greater than the minimum time.

In certain embodiments, the dry powder may be reconstituted for four hours before being administered to a subject.

As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except in so far as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with dry powder without causing any undesirable biological effects or interacting in a deleterious manner with any of the other components of the pharmaceutical composition in which it is contained.

A formulation may be conveniently presented in unit dosage form and may be prepared by methods well known in the art of pharmacy. Methods of preparing a composition with a pharmaceutically acceptable carrier include the step of bringing the dry powder into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of the vaccine administered can vary depending on various factors including, but not limited to, the weight, physical condition, and/or age of the subject, and/or the route of administration. Thus, the absolute amount of the vaccine included in a given unit dosage form can vary widely, and depends upon factors such as the species, age, weight and physical condition of the subject, and/or the method of administration. Accordingly, it is not practical to set forth generally the amount that constitutes an amount of the vaccine effective for all possible applications. Those of ordinary skill in the art, however, can readily determine the appropriate amount with due consideration of such factors.

In some embodiments, the method can include administering sufficient vaccine to provide a dose of, for example, from about 100 ng/kg to about 50 mg/kg to the subject, although in some embodiments the methods may be performed by administering vaccine in a dose outside this range. In some of these embodiments, the method includes administering sufficient vaccine to provide a dose of from about 10 µg/kg to about 5 mg/kg to the subject, for example, a dose of from about 100 µg/kg to about 1 mg/kg.

Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184.

In some embodiments, the method can include administering sufficient vaccine to provide a dose of, for example, from about 0.01 mg/m$^2$ to about 10 mg/m$^2$.

In some embodiments, vaccine may be administered, for example, from a single dose to multiple doses per week, although in some embodiments the method can be performed by administering the vaccine at a frequency outside this range. In certain embodiments, the vaccine may be administered from about once per month to about five times per week.

The dry powder vaccine may be stored prior to being administered to a subject. In some cases, the dry powder vaccine may be stored without refrigeration for a minimum of at least three months such as, for example, at least four months, at least five months, at least six months, at least seven months, at least eight months, at least nine months, at least ten months, at least 11 months, at least 12 months, at least 13 months, at least 14 months, or at least 15 months.

In some cases, the dry powder vaccine may be stored without refrigeration for as long as the vaccine retains an effective degree of potency. Methods for testing the potency of a vaccine composition are conventional and well-known to those of ordinary skill in the art. In some cases, the dry powder vaccine may be stored without refrigeration for maximum of no more than 10 years such as, for example, no more than five years, no more than four years, no more than three years, no more than two years, no more than 18 months, no more than 16 months, no more than 15 months, no more than 14 months, no more than 13 months, no more than 12, months, no more than 11 months, or no more than ten months.

In some cases, the dry powder vaccine may be stored without refrigeration for a minimum of at least two months, at least three months, at least six months, at least nine months, at least one year, at least 13 months, at least 14 months, or at least 15 months.

In some embodiments, the dry powder vaccine may be stored without refrigeration for a period within a range having endpoints defined by any minimum period defined above and any maximum period greater than the minimum period.

As used herein, the term "without refrigeration" includes storage conditions of at least 4° C. such as, for example, at least 10° C., at least 15° C., conventional room temperature (e.g., 16° C.-26° C.), at least 30° C., or normal human body temperature (37° C.).

In some cases, the dry powder may be stored with an inert gas (e.g., $N_2$, Ar, Kr, Xe), an $O_2$ scavenger (e.g., any pharmaceutical grade $O_2$ scavenger such as, for example, PHARMAKEEP (Clariant Corp., Charlotte, N.C.)), and/or a desiccant (e.g., activated charcoal, calcium sulfate, calcium chloride, cobalt chloride, a molecular sieve, or any food grade silica desiccant). In some embodiments, the dry powder may be stored with an $O_2$ scavenger. In other embodiments, the dry powder may be stored with a desiccant. In still other embodiments, the dry powder may be stored with an $O_2$ scavenger and a desiccant.

In the preceding description, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiment can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1—Spray Drying Formulation of Live
*Listeria monocytogenes* Vaccine

Recombinant attenuated *Listeria* monocytogenes (Lm) expressing *Francisella tularensis* immunoprotective antigen IglC were grown in YNG media (yeast extract 25 g/L, $KH_2PO_4$ 9 g/L, pH 7.2) at 37° C. for different time periods with shaking. To prepare *Listeria monocytogenes* for spray drying, the culture was centrifuged (4000×g and 4° C. for 30 min) and the resultant pellet was washed by suspending in a volume of sterile spray drying solution equal to the culture volume. The spray drying solution consisted of 2.05% (w/v) solution of five excipients: 85.4% Mannitol, 1.71% Trehalose, 0.853% Dextran, 7.85% Leucine and 4.27% Inositol. The *Listeria monocytogenes* suspension was centrifuged again and the resulting pellet was again re-suspended in 70 ml to 100 ml of the spray drying solution. A Buchi Mini Spray Dryer B-290 was used for spray drying.

Example 2—Characterization of Dry Powder Live
*Listeria monocytogenes* Vaccine

Figure 3:
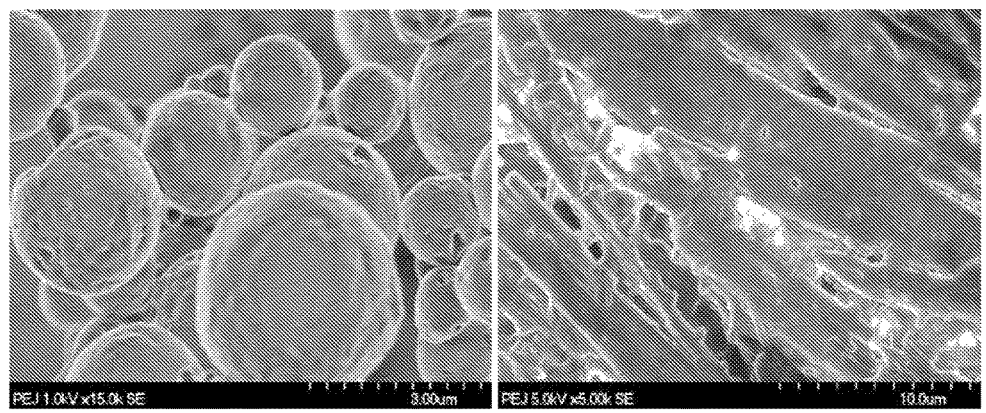
FIG. 3. Scanning electron micrographs of (A) spray dried *Listeria monocytogenes* dry powder vaccines and (B) same vaccine powders were dissolved; *Listeria monocytogenes* bacterial cells were observed to be embedded.
Figure 4:
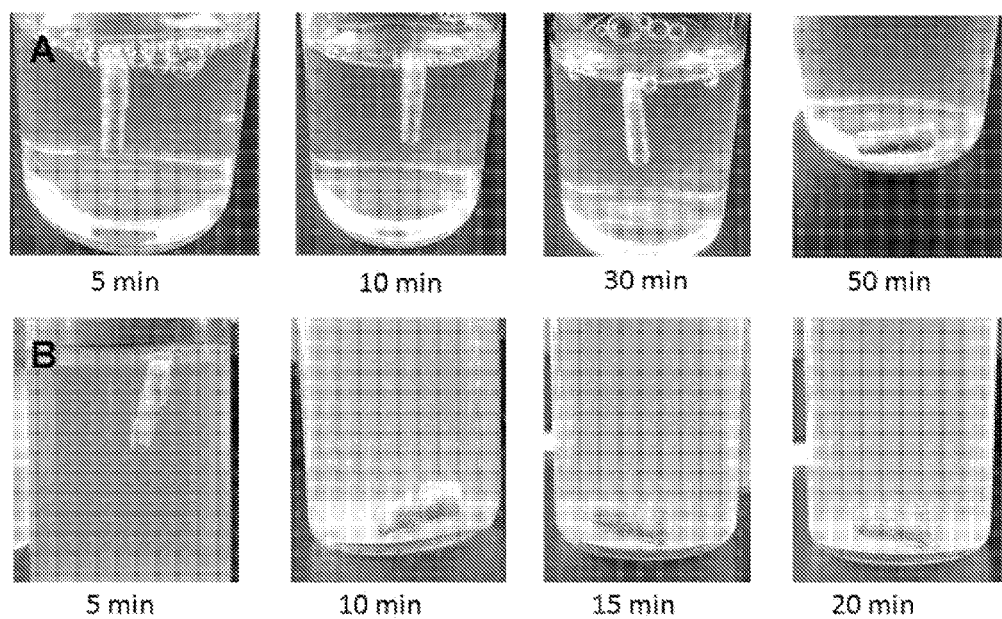
FIG. 4. Integrity of (A) enteric coated capsules in simulated gastric fluid and followed by immersion in simulated intestinal fluid compared to (B) capsules lacking an enteric coating.

The spray dried live powder vaccines were characterized for their particle size distribution using laser diffraction system and a scanning electron microscopy (SEM, JEOL 5800LV) was used to examine the morphology and also further ascertain size of the spray-dried powders. Results are shown in FIG. 3 and FIG. 4.

Figure 2:
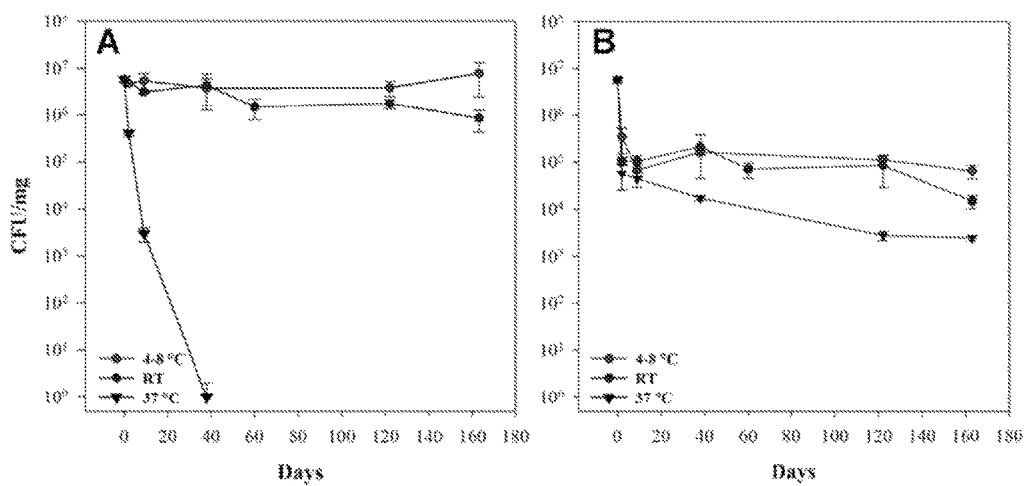
FIG. 2. Viability based on CFUs of moisture protected *Listeria monocytogenes* dry powder vaccine (A) stored inside a desiccator, (B) stored in a desiccator and with a desiccant inside each vial.

For long-term stability studies of dry powder *Listeria* monocytogenes vaccine, CFUs were counted after serial dilution and subsequent plating. For the stability study, the vaccine powders were divided into three aliquots and stored at 4° C., room temperature (22±2° C.), and at 37° C. Furthermore for moisture protection studies, each of the above mentioned groups were further divided into two treatments, one stored in a desiccators (MP) and the second treatment samples were stored in a desiccator as above, but with a desiccant inside the vial (MP-WD). Results are shown in FIG. 1 and FIG. 2.

Example 3—Characterization of Various
Formulations of Dry Powder *Listeria
monocytogenes* Vaccine Long-term stability studies of dry powder *Listeria monocytogenes* vaccine, CFUs were counted after serial dilution and subsequent plating. For the stability study, the dry powder vaccine formulations shown in Table 2 were divided into three aliquots and stored at 4° C., at 37° C. in a nitrogen environment (N only), or at 37° C. in a nitrogen environment with an $O_2$ scavenger and a desiccant (N+OsD). Results are shown in FIG. 6.

Figure 7:
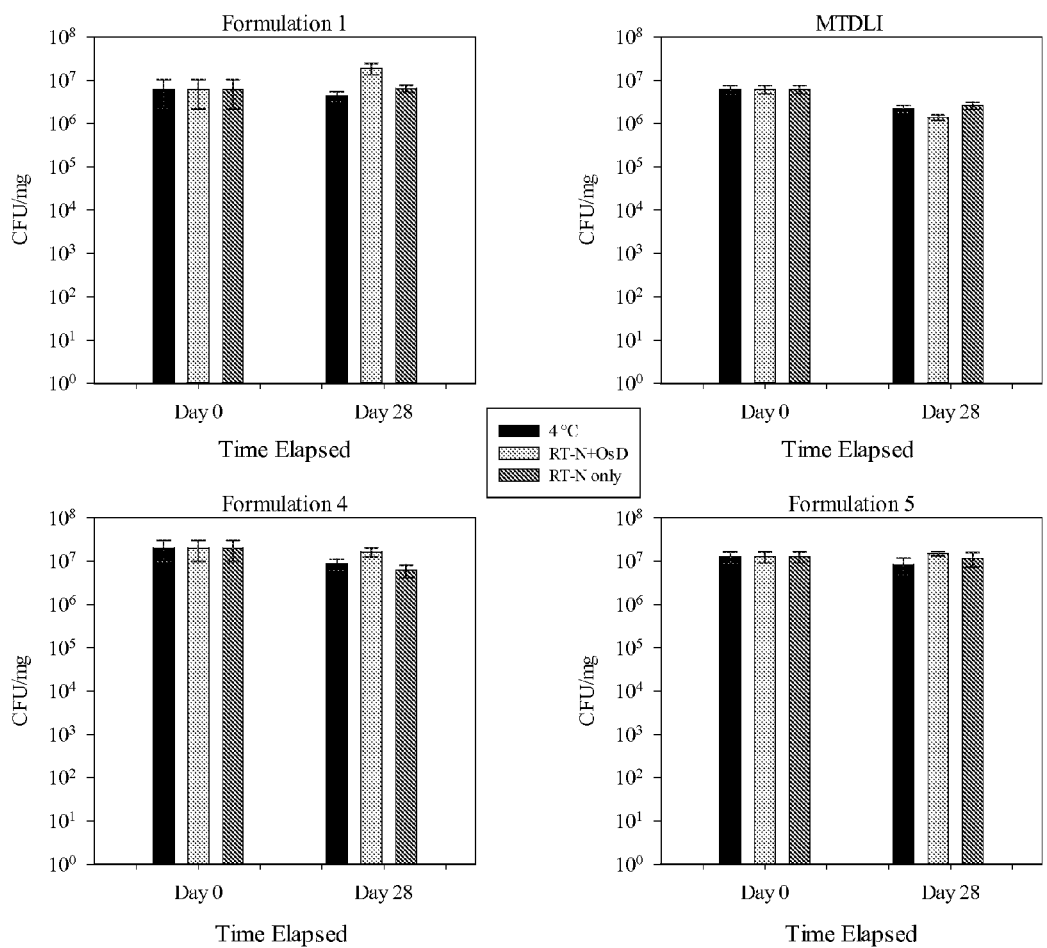
FIG. 7. Survival of spray dried *Listeria* vaccine stored at room temperature (RT; 22-24° C.). At storage between 22° C. and 24° C., dry powder *Listeria* showed viability in both '$N_2$ only' and '$N_2$ with $O_2$ scavenger and desiccant'.
Figure 8:
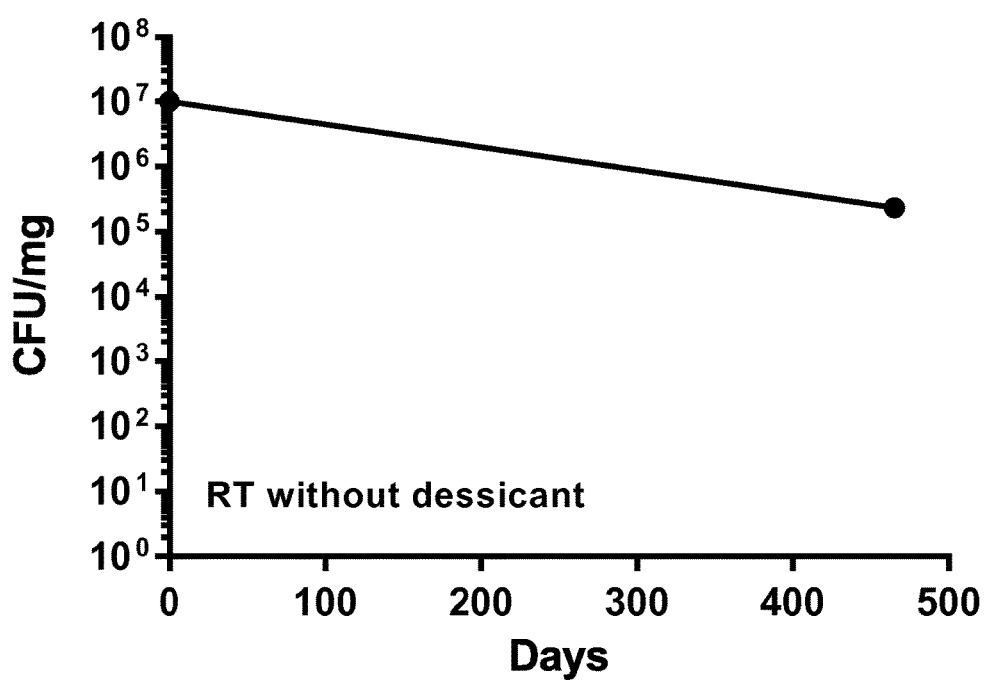
FIG. 8. *Listeria monocytogenes* viability in MTDLI formulation (Formulation 3, Table 2) after storage for 15.5 months at Room Temperature.

Survival of spray dried *Listeria* vaccine stored at 22-24° C. (RT), either in a nitrogen environment (RT-N only) or in a nitrogen environment with an $O_2$ scavenger and a desiccant (RT-N+OsD). Results are shown in FIG. 7.

*Listeria monocytogenes* viability in MTDLI formulation (Formulation 3, Table 2) after storage for 15.5 months at 22-24° C. (RT), without a desiccant.

EXEMPLARY EMBODIMENTS

Embodiment 1

A composition comprising: a dry powder matrix; and a bacterium disposed within the matrix.

Embodiment 2

The composition of Embodiment 1 wherein the bacterium is genetically modified to express at least one heterologous antigen.

Embodiment 3

The composition of Embodiment 1 wherein the bacterium is genetically modified to increase expression of an endogenous secretory antigen.

Embodiment 4

The composition of any preceding Embodiment wherein the bacterium comprises an attenuated *Listeria* monocytogenes.

Embodiment 5

The composition of any preceding Embodiment further comprising a storage satchel.

Embodiment 6

The composition of Embodiment 5 wherein the storage satchel comprises an $O_2$ scavenger or a desiccant.

Embodiment 7

A method comprising: mixing a bacterium that expresses at least one antigen in a solution that comprises at least one amino acid and at least one saccharide; and spray drying the mixture to form a dry powder.

Embodiment 8

The method of Embodiment 7 wherein the bacterium comprises an attenuated *Listeria monocytogenes* genetically modified to express at least one heterologous antigen.

Embodiment 9

The method of Embodiment 8 wherein the heterologous polypeptide comprises a *Francisella tularensis* antigen.

Embodiment 10

The method of Embodiment 9 wherein the *Francisella tularensis* antigen comprises Ig1C.

Embodiment 11

The method of any one of Embodiments 7-10 further comprising storing the dry powder without refrigeration for at least three months.

Embodiment 12

The method of Embodiment 11 wherein the dry powder is stored without refrigeration for at least 15 months.

Embodiment 13

The method of Embodiment 11 or 12 wherein the dry powder is stored in the presence of an $O_2$ scavenger or a desiccant.

Embodiment 14

The method of Embodiment 13 wherein the dry powder is stored in the presence of an $O_2$ scavenger and a desiccant.

Embodiment 15

The method of any one of Embodiments 11-14 wherein the dry powder is stored in the presence of an inert gas.

Embodiment 16

The method of any one of Embodiment 7-15 further comprising administering the dry powder to a subject.

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
   mixing a bacterium that expresses at least one antigen in a suspension that comprises at least one amino acid and at least one saccharide;
   spray drying the mixture to form a dry powder; and
   storing the dry powder without refrigeration for at least two months in the presence of:
   an $O_2$ scavenger,
   a desiccant, or
   an inert gas.

2. The method of claim 1 wherein the bacterium comprises an attenuated *Listeria monocytogenes* genetically modified to express at least one heterologous antigen.

3. The method of claim 2 wherein the heterologous polypeptide comprises a *Francisella tularensis* antigen.

4. The method of claim 3 wherein the *Francisella tularensis* antigen comprises Ig1C.

5. The method of claim 1 wherein the dry powder is stored without refrigeration for at least 15 months.

6. The method of claim 1 wherein the dry powder is stored in the presence of an $O_2$ scavenger or a desiccant.

7. The method of claim 1 wherein the dry powder is stored in the presence of an $O_2$ scavenger and a desiccant.

8. The method of claim 1 wherein the dry powder is stored in the presence of an inert gas.

9. The method of claim 1 further comprising administering the dry powder to a subject.

10. The method of claim 1 wherein the bacterium is attenuated.

11. The method of claim 1 wherein the bacterium genetically modified to express at least one heterologous antigen.

12. The method of claim 1 wherein the dry powder is stored in the presence of an $O_2$ scavenger, a desiccant, and an inert gas.

\* \* \* \* \*